US012744107B2

(12) United States Patent
Wu et al.

(10) Patent No.: US 12,744,107 B2
(45) Date of Patent: Sep. 22, 2026

(54) SYSTEM AND METHOD FOR NUCLEOTIDE ANALYSIS AND PREDICTION OF DISEASE RISK

(71) Applicant: MIRATERRA INC., Lewes, DE (US)

(72) Inventors: Diane Wu, San Francisco, CA (US); Poornima Parameswaran, Menlo Park, CA (US)

(73) Assignee: MIRATERRA INC., Lewes, DE (US)

( * ) Notice: Subject to any disclaimer, the term of this patent is extended or adjusted under 35 U.S.C. 154(b) by 956 days.

(21) Appl. No.: 16/937,578

(22) Filed: Jul. 23, 2020

(65) Prior Publication Data

US 2020/0357485 A1 Nov. 12, 2020

Related U.S. Application Data

(63) Continuation of application No. 15/288,731, filed on Oct. 7, 2016, now Pat. No. 10,762,982.

(60) Provisional application No. 62/238,615, filed on Oct. 7, 2015.

(51) Int. Cl.

*G16B 40/00* (2019.01)
*G06N 20/00* (2019.01)
*G16B 25/00* (2019.01)
*G16H 50/20* (2018.01)

(52) U.S. Cl.

CPC ............. *G16B 40/00* (2019.02); *G06N 20/00* (2019.01); *G16B 25/00* (2019.02); *G16H 50/20* (2018.01)

(58) Field of Classification Search

CPC ........ G16B 40/00; G16B 25/00; G16H 50/20; G06N 20/00

See application file for complete search history.

(56) References Cited

U.S. PATENT DOCUMENTS 7,005,257 B1 2/2006 Haas et al.
7,058,616 B1 * 6/2006 Larder .................. G16B 20/20 435/5
10,395,115 B2 8/2019 Kumar et al.
2003/0190603 A1 10/2003 Larder et al.
2006/0160071 A1 7/2006 Heckerman et al.
2007/0130633 A1 6/2007 Urban et al.
2012/0310863 A1 * 12/2012 Crockett ................ G16B 20/20 702/19
2013/0259899 A1 10/2013 Allen-Vercoe et al.
2014/0127718 A1 * 5/2014 Ma .................. G01N 33/56911 435/7.1
2014/0162274 A1 6/2014 Kunin et al.
2014/0213770 A1 7/2014 Dong et al.

(Continued)

FOREIGN PATENT DOCUMENTS

WO WO-0070340 A2 * 11/2000 ......... G01N 33/6803

OTHER PUBLICATIONS

Kennedy et al. (How Flickr Helps US Make Sense of the World: Context and Content in Community-Contributed Media Collections, Sep. 2007, pp. 631-640) (Year: 2007).*

(Continued)

*Primary Examiner* — George Giroux
(74) *Attorney, Agent, or Firm* — FBT Gibbons LLP

(57) ABSTRACT

A system and method for the detection of pathogens and other microbes using nucleotide analysis is described. Aligned and unaligned nucleotide sequences are utilized to predict the presence or absence of pathogens and other microbes.

20 Claims, 15 Drawing Sheets

(56) References Cited

U.S. PATENT DOCUMENTS

| | | | | |
|---|---|---|---|---|
| 2015/0056613 | A1* | 2/2015 | Kural | G16B 30/10 435/6.11 |
| 2015/0267191 | A1 | 9/2015 | Steelman et al. | |
| 2015/0284810 | A1 | 10/2015 | Knight et al. | |
| 2016/0103958 | A1 | 4/2016 | Hebert et al. | |
| 2016/0148104 | A1* | 5/2016 | Itzhaky | G06N 3/08 706/12 |
| 2017/0039316 | A1 | 2/2017 | Fofanov et al. | |
| 2017/0213083 | A1 | 7/2017 | Shriver et al. | |
| 2019/0227046 | A1 | 7/2019 | Parameswaran et al. | |

OTHER PUBLICATIONS

Nielsen et al. (Microorganisms as indicators of soil health, Jan. 2002, pp. 0-82) (Year: 2002).*

Cretoiu et al. (A novel salt-tolerant chitobiosidase discovered by genetic screening of a metagenomic library derived from chitin-amended agricultural soil, Apr. 2015, pp. 1-18) (Year: 2015).*

Van Elsas et al. (The metagenomics of disease-suppressive soils—experiments from the Metacontrol probje4ct, Sep. 2008, pp. 591-601) (Year: 2008).*

Lawrence, C. E. et al. “An Expectation Maximization (EM) Algorithm for the Identification and Characterization of Common Sites in Unaligned Biopolymer Sequences.” Proteins: Structure, Function, and Genetics, vol. 7, No. 1, 1990, pp. 41-51.

Loewenstern, D. et al. “DNA Sequence Classification Using Compression-Based Induction.” Rutgers University Libraries, May 1995, pp. 1-12.

United States Office Action, U.S. Appl. No. 15/288,731, filed Apr. 2, 2019, 22 pages.

United States Office Action, U.S. Appl. No. 15/288,731, filed Aug. 30, 2019, 16 pages.

* cited by examiner

SYSTEM AND METHOD FOR NUCLEOTIDE ANALYSIS AND PREDICTION OF DISEASE RISK

CROSS-REFERENCE TO RELATED APPLICATIONS

This application is a continuation of U.S. application Ser. No. 15/288,731, filed on Oct. 7, 2016, which claims the benefit of U.S. Provisional Application Ser. No. 62/238,615, filed on Oct. 7, 2015, all of which are incorporated herein by reference in their entirety for all purposes.

FIELD

The present invention relates to nucleotide analytics, and more particularly to sequence population analytics.

BACKGROUND

Nucleic acids, including deoxyribonucleic acid (DNA) and ribonucleic acid (RNA), are made from nucleotides and, along with proteins, are present in all known forms of life. They function in encoding, transmitting and expressing genetic information and life forms differ by the order of nucleotides within a DNA or RNA molecule, known as the nucleic acid sequence. Determining the nucleic acids sequences in a sample is known as sequencing.

It is possible to determine the type(s) of life form(s) present in a sample by isolating the genetic material of the life form(s) from the sample, determining the nucleic acid sequence of that genetic material, and using a variety of computational or algorithmic methods to determine the likely sources of that genetic material. Nucleic acid sequences matched to known genomes to determine the type of life form(s) present in the sample.

A microorganism is microscopic organism, such as a bacterium, protozoa, or fungus. A pathogen may be a microbial organism (e.g., a bacterium, phytoplasma, virus, viroid, protozoan, rickettsia, or fungus). Additionally, a pathogen may be a bacterium, phytoplasma, virus, viroid, protozoan, rickettsia, fungus, helminth, parasite, or pest. A microbe is a microorganism, such as a bacterium, that, e.g., causes a disease or fermentation. Interactions between microbes may be exhibit commensalism (one benefits from the other without affecting the other), mutualism (mutually beneficial), amensalism (one is harmed while the other is unaffected), or parasitism (one benefits while the other is harmed) relationships with other organisms. Microbes may change how they affect other organisms, such as a commensal microbe becoming pathogenic under stress. For example, a particular bacteria may be harmonious with a particular fungi, but when the bacteria is stressed and dies off, the fungi may become pathogenic. A microbe that is pathogenic is a microorganism that can produce disease. Typically, a pathogen is an infectious agent such as a virus, bacterium, prion, fungus, viroid, protozoa nematode or parasite families that causes disease in its host. While there are thousands of species of pathogens, only a few dozen pathogens have been sequenced or even studied. It is also possible to have pathogenic host genes.

The nucleic acids of humans is a frequent focus for studies and out of those studies have come tools and processes to make further study of humans much easier. However, assumptions made about similarities of nucleic acid sequences across the human race may not apply to microbes. Similar kinds of assumptions are invalid when sequencing non-human material, making the use of most existing methods and tools inappropriate for non-human study.

When checking a sample for the presence or absence of a particular microbe, existing tools may count the number of nucleic acid sequences in the sample that align 100% to known nucleic acid sequences of that microbe. The nucleic acid sequences in the sample that do not align to that microbe, called unaligned sequences, are not used or even generally retained. Nucleic acid sequences may not align for many reasons, such as the presence of merely one or more mutations that are undetectable by the particular bioinformatics alignment algorithm used.

BRIEF DESCRIPTION OF THE FIGURES

The present invention is illustrated by way of example, and not by way of limitation, in the figures of the accompanying drawings and in which like reference numerals refer to similar elements and in which.

DETAILED DESCRIPTION

Figure 1:
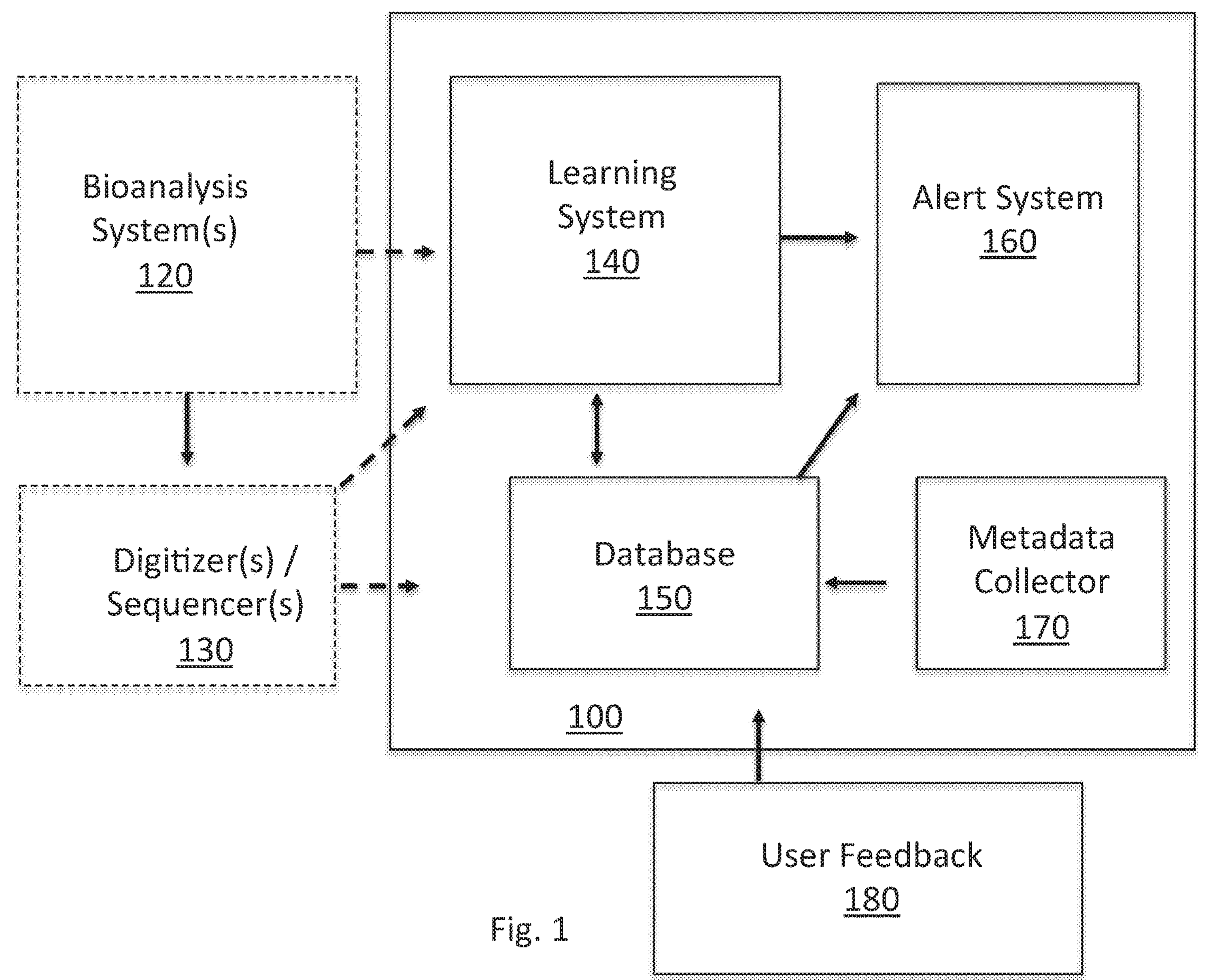
FIG. 1 is a system diagram of one embodiment of a nucleotide analysis system.

Using novel tools and systems for quantifying and analyzing samples containing aggregated groups of sequences from nucleic acids extracted from microbes, we can overcome the deficiencies in the current art as well as provide new areas of information about microbes. The system and method in one embodiment, associates, both directly and indirectly, pools of sequences to biological organisms and biological states, utilizing both known and unknown portions of sequences to determine qualitative and quantitative traits related to the samples. Such traits may include disease state of the samples from which the microbes originated, likelihood to cause disease in organisms associated with the samples from which the microbes originated, the temporal or geographical distribution of organisms or of disease outcomes, and transmission pathways of pathogenic organisms Determination of microbe populations can lead to insights about the health or disease states of one or more organisms or one or more populations of organisms or a location. For example, the air may be tested for fungus to determine a risk of fungal disease to one or more types of plants in that area. Water circulating in a greenhouse may be tested to determine the disease state of plants in the greenhouse. Pests in a field may be tested to determine which diseases are being actively spread by vectors. Seawater or water filters may be tested to determine whether there exists a disease risk to agriculture.

Sewage may be tested to determine which diseases are being excreted by the human population to, for example, gain insight into the population health. Pathogens are usually excreted in large amounts before the first symptoms of disease become apparent, allowing for early asymptomatic detection of disease. Livestock feed may be tested to determine the risk of pathogen infection to livestock or to determine the balance of beneficial microbes for livestock health. Food such as vegetables may be tested to determine the risk of food-borne diseases that pose a risk to human health when ingested. Blood, lymph, urine, fecal matter, or other bodily fluid or excreta from an animal may be tested to determine the infections state of the animal or the balance of beneficial and harmful microbes associated with the animal. This list of potential sources of material for testing is not exhaustive, and any materials which can contain pathogens or microbes may be tested.

Identification of microbe strain, sub-strain, and nucleic acid identity can also yield statistically significant information on the path and evolution of the microbe. This field of study is called molecular epidemiology. Note, that while some pathogens are not microbes and pathogenic host genes are not microbes, they may be sequenced and analyzed in helpful ways with the present invention. Therefore, the term "microbe" and "microbes" as used herein includes non-microbial pathogens, organisms, byproducts of a pest or another organism and pathogenic host genes additionally.

Identification of microbe sequences can also yield statistically robust conclusions regarding the origin of the microbes, leading to insights and conclusions about the health of the organisms from which the microbes arose. For example, a sewage sample contains microbes, which contain genetic material, that can be used to track the evolution of microbes from sewage sources. In another example, genomic characterization of salmonella from multiple infected individuals can determine the number of contaminating origins. Genomic characterization of the food source (e.g. spinach farm) can yield epidemiological information that can triage the origin of infection with statistical confidence.

FIG. 1 is a system diagram of one embodiment of the nucleotide analysis system. Nucleotide sampling system 100 receives information from one or more bioanalysis systems 120 and one or more digitizers/sequencers 130. Sampling system 100 may in one embodiment receive user feedback 180. Nucleotide sampling system 100 in one embodiment includes learning system 140, database 150, alert system 160, and metadata collector 170. The nucleotide sampling system 100 in one embodiment comprises one or more processors, which may be accessed via a network, or may be distributed. Processors may also communicate with storage, used for database 150.

Methods and systems within bioanalysis system 120 are used for separating and utilizing portions of a biological sample to identify nucleic acid sequences of nucleotides present in the sample. For example, Trizol extraction for DNA isolation, followed by PCR for DNA amplification, followed by sequencing may be used by the bioanalysis system 120. The bioanalysis system may also utilize commercially available nucleic acid extraction and purification kits and buffers.

Information from bioanalysis system 120 is digitized by digitizer 130. Digitizer 130 captures information regarding the nucleic acid sequences in the output from bioanalysis system 120 and may store information in database 150. This information can provide data to infer the quantity of the microbes, the identity of the microbes, the diversity and evolutionary pressures the microbes were under prior to entering the system, as well as other information that might be present in the sample, as will be described below. Other information may include the host genome for host genomic characterization, vector genomic information for determining the presence of vectors in the sample, which is a risk factor for disease transmission. Genomic information may include DNA, RNA, small RNA, or any other "sequenceable" nucleic acid. In addition to nucleic acids, bioanalysis system 120 can be replaced by or complemented with another bioanalysis system 120 to provide additional information to an additional digitizer 130. This additional digitizer may also store data into database 150. Additional bioanalysis systems 120 may determine, for example, the metabolomics of the sample composition, the protein population in the sample, the physical properties of the sample (e.g. density, moisture level and pH of soil, which are strong indicators for disease). In one embodiment, a single sample may be processed by multiple bioanalysis systems 120.

Digitized information from database 150, provided by the one or more digitizers may be applied to learning system 140. In one embodiment, learning system 140 is a deep learning system. In one embodiment, learning system 140 is a machine learning system. Both within each sample and across samples, learning system 140 operates to discern patterns in the digitized information.

Deep learning system 140, in one embodiment, is configured as a multi-layered neural network where the connections in each layer reduce in size from layer to layer. In one embodiment, deep learning system 140 is trained by feeding in nucleic acid sequences as the input and phenotypic characteristics as output. Weights for the connections between nodes may be randomly or systematically initiated, and the system is allowed to converge to minimize error of predictions. Inputs to the deep learning system 140 may specifically include nucleic acid sequences representing the sample to be used, as well as metadata associated with the sample such as climate information, geographical information, soil treatment history and plant genetics. In one embodiment, deep learning system is implemented using a cloud-based infrastructure.

Database 150 is used to store information for each sample, across a plurality of samples, and metadata related to samples, in addition to storing patterns and correlations obtained from learning system 140. Alert system 160 is used to provide insight and output to users, such as reports, texts, and web-page updates. In one embodiment, the alert system 160 may provide simple predictions about the organisms identified. In one embodiment, the alert system 160 may provide predictions on the likelihood for disease incidence or measurements for plant health. FIGS. 3A-3G are example alert system outputs in accordance with embodiments of the nucleotide analysis system.

When sequencing microbes from the environment, such as microbes in a plant or in the soil, it is impractical to isolate each individual microbe to then sequence the genome for that microbe. The sample that is sequenced may contain many microbes within and across families of microbes. Therefore, sequencing the sample as a whole results in a "collective genome" representing the variety of microbes in the sample. Portions of that collective genome that may correspond (or align) to known (or previously sequenced) microbes. Portions of that collective genome may map to more than one species, meaning that they are shared regions that are conserved across species. Portions of that collective genome will not align to any known microbe, as those unknown microbes have not been sequenced or possibly even studied. Additionally, these unaligned sequences may also come from known microbes whose genomes have not been sufficiently sequenced, or whose genome has evolved considerably from the sequenced strain stored the database or known to other researchers. Note that, while many nucleic acid sequences might be unaligned, the order of nucleotides comprising the unaligned sequences themselves are known.

By way of example, if a soil sample contains 1000 microbes, some number (for example, 3) of the microbes will be known with known nucleic acid sequences, but the rest of the microbes will be unknown (or unaligned). If 100,000 nucleic acid sequences are found in the soil sample, it will be unclear which of those sequences align with each of the rest of the 997 unknown microbes. In other words, if you are simultaneously putting together 1000 puzzles having similar pictures, where some puzzles have several missing pieces and all the puzzle pieces are mixed together, it can be difficult to determine which puzzle piece goes with which puzzle. However, even without isolating unknown microbes, valuable information about the sample can be extracted from this collective genome.

Figure 2:
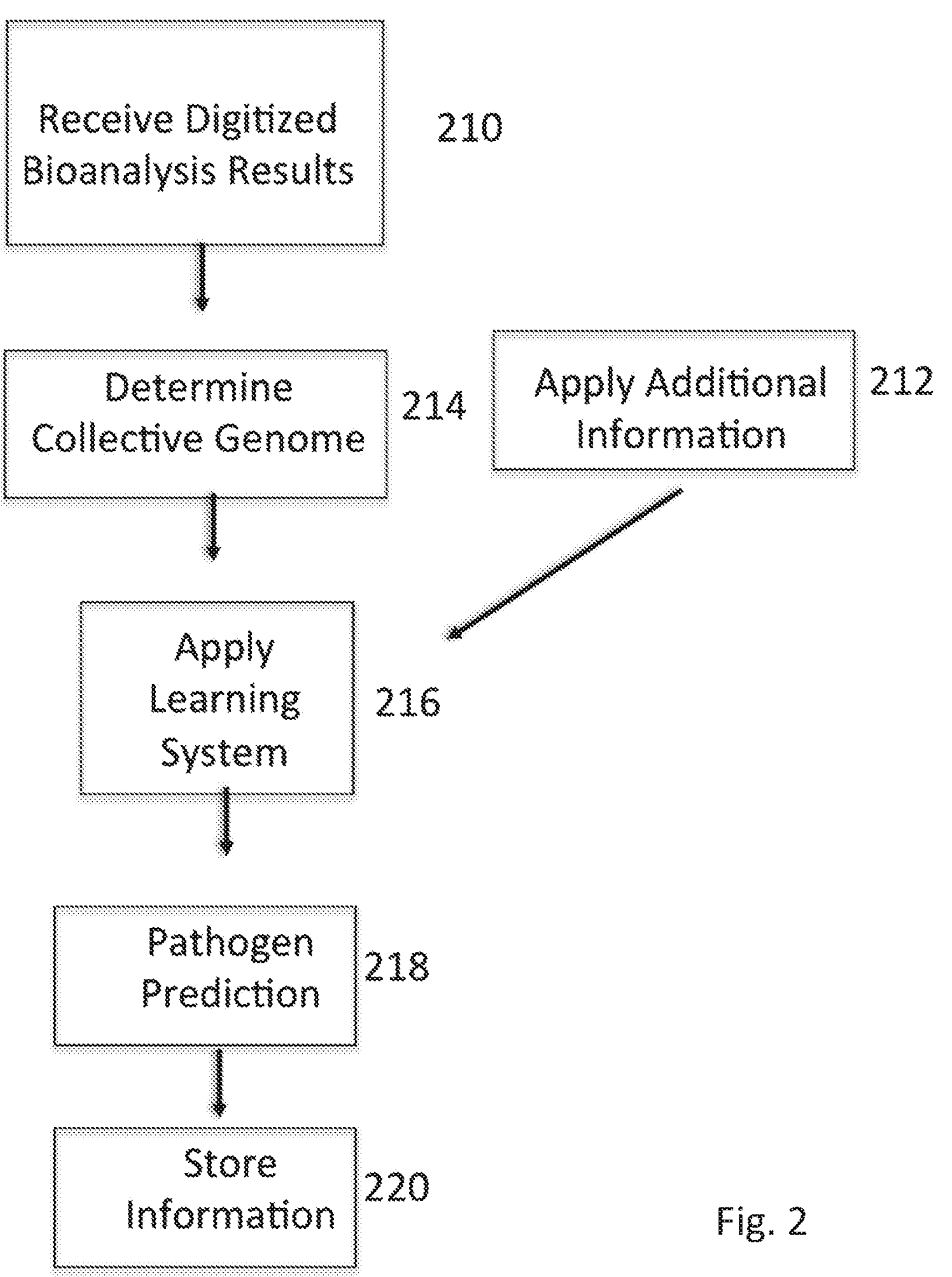
FIG. 2 is a flowchart of one embodiment of utilizing the present nucleotide analysis system.
Figure 3A:
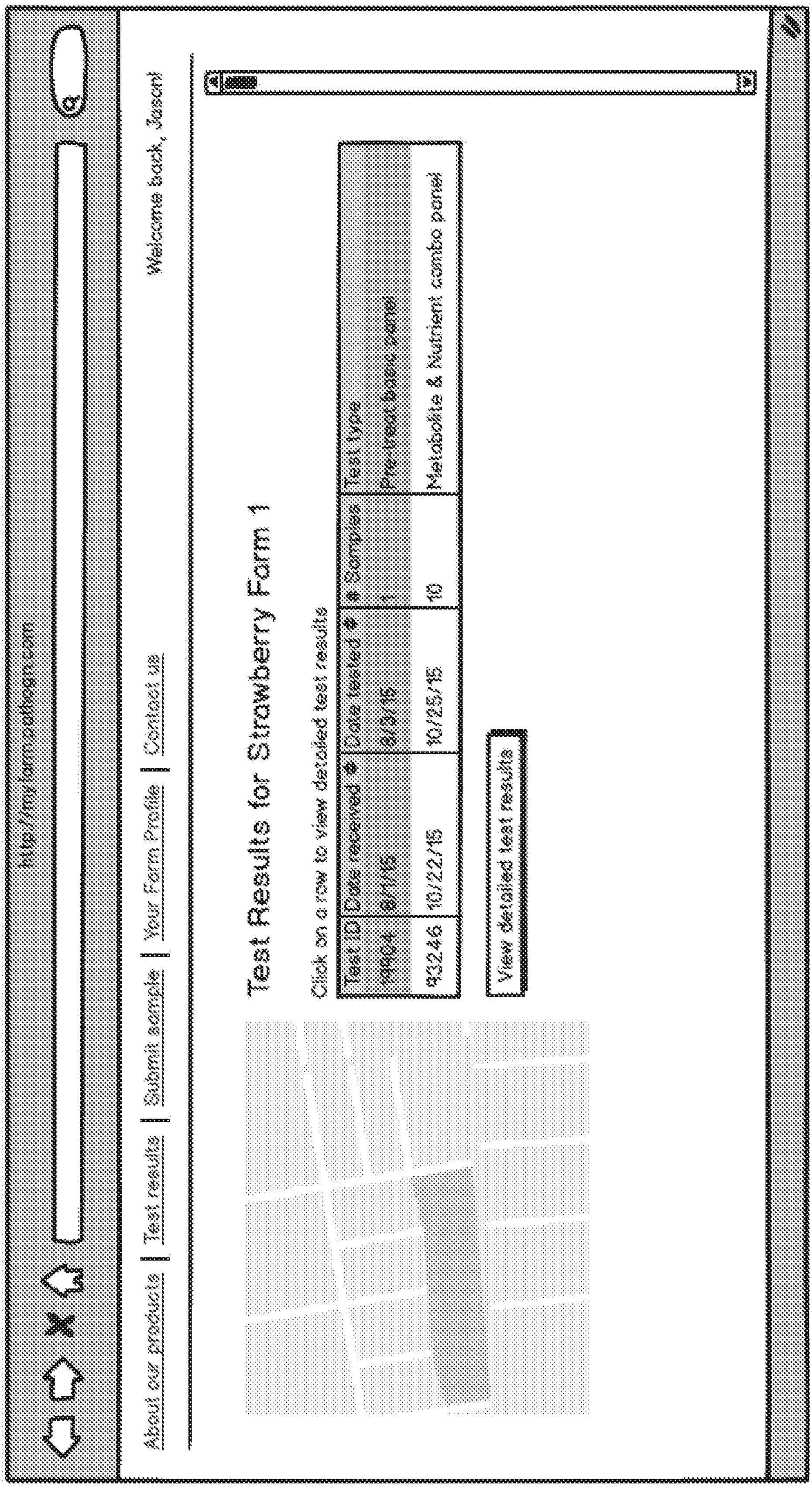
FIGS. 3A, 3B, 3C, 3D, 3E, 3F, and 3G are example alert system outputs in accordance with embodiments of the nucleotide analysis system.
Figure 3B:
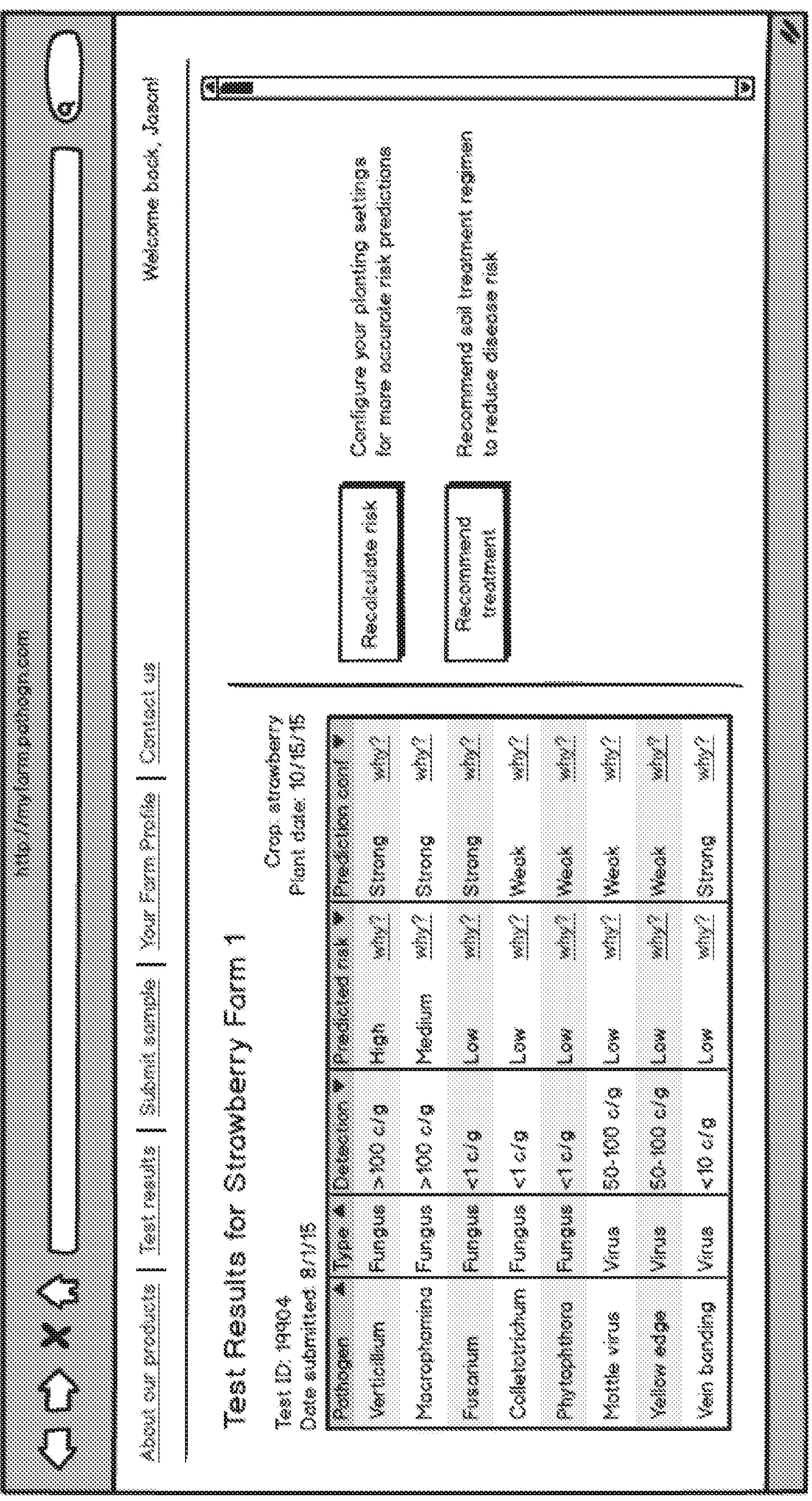
Figure 3C:
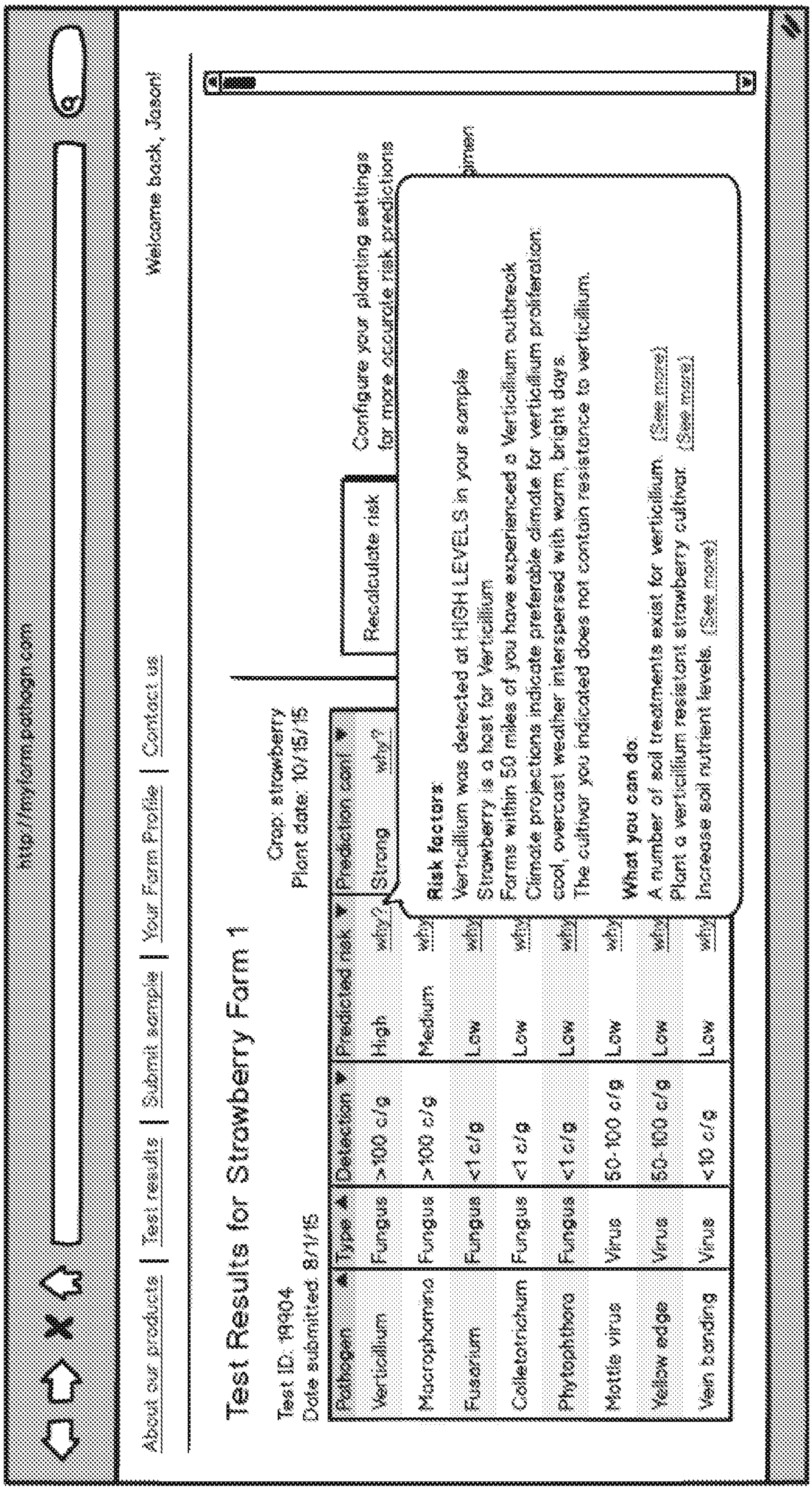
Figure 3D:
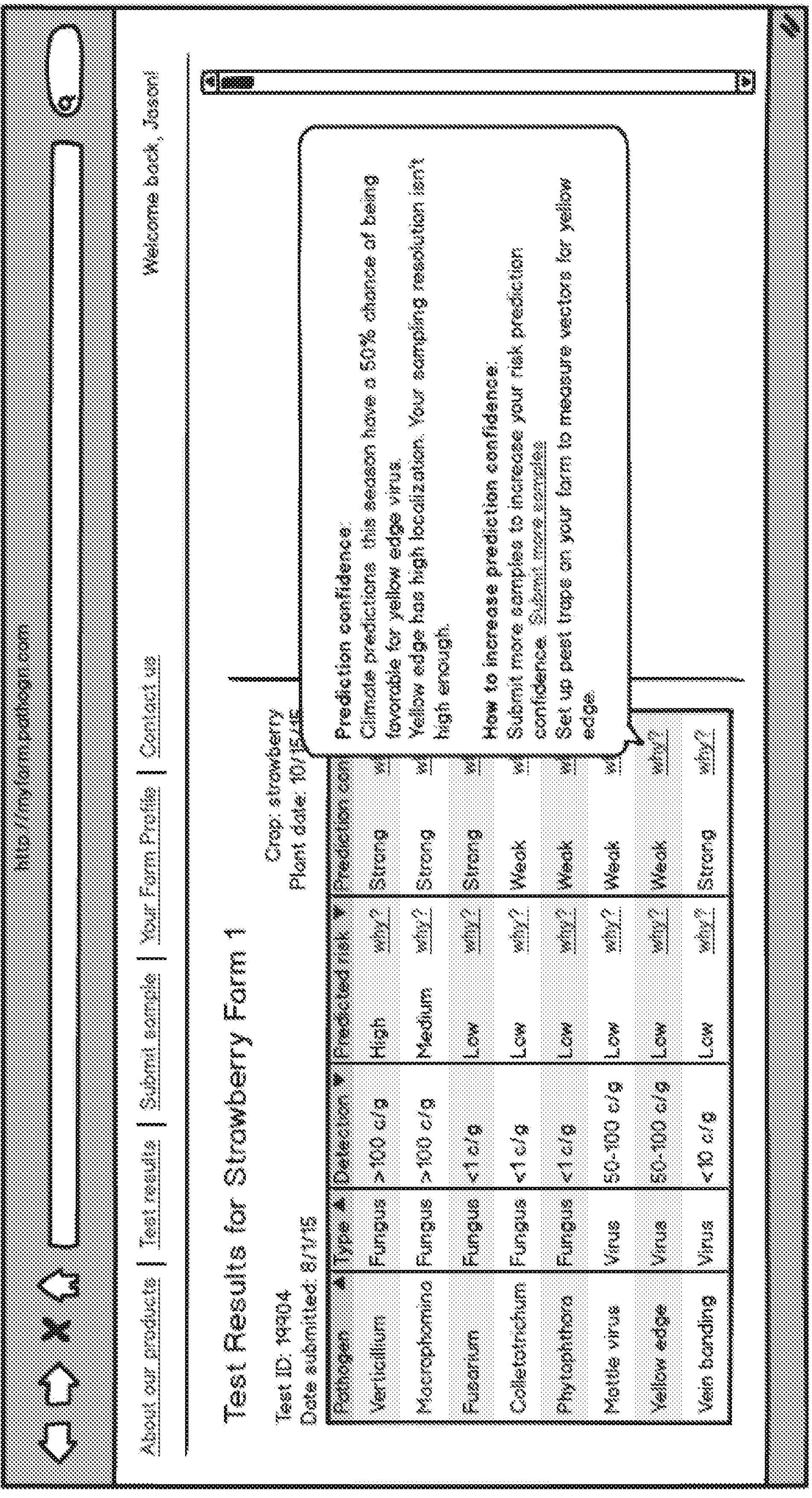
Figure 3E:
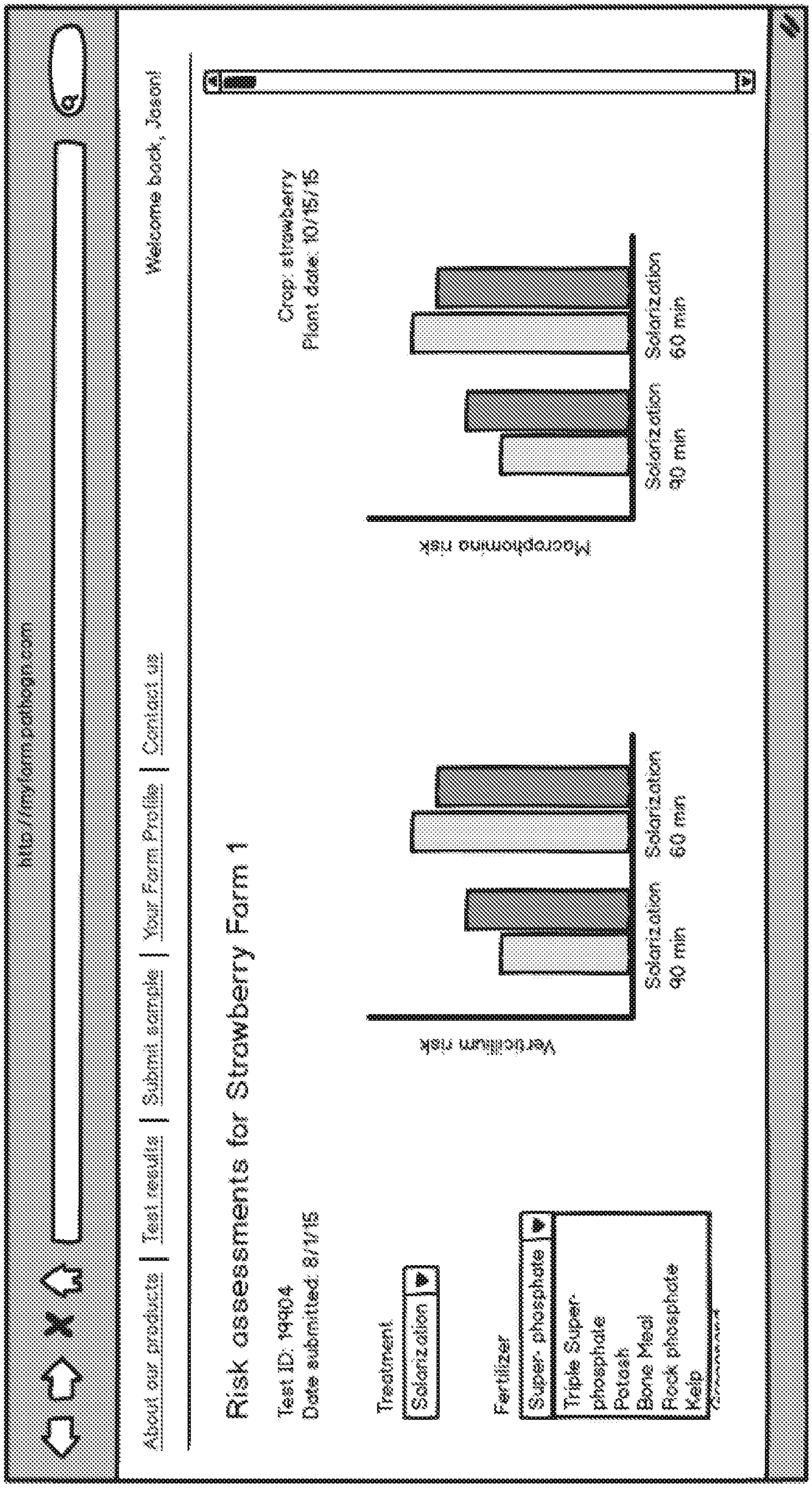
Figure 3F:
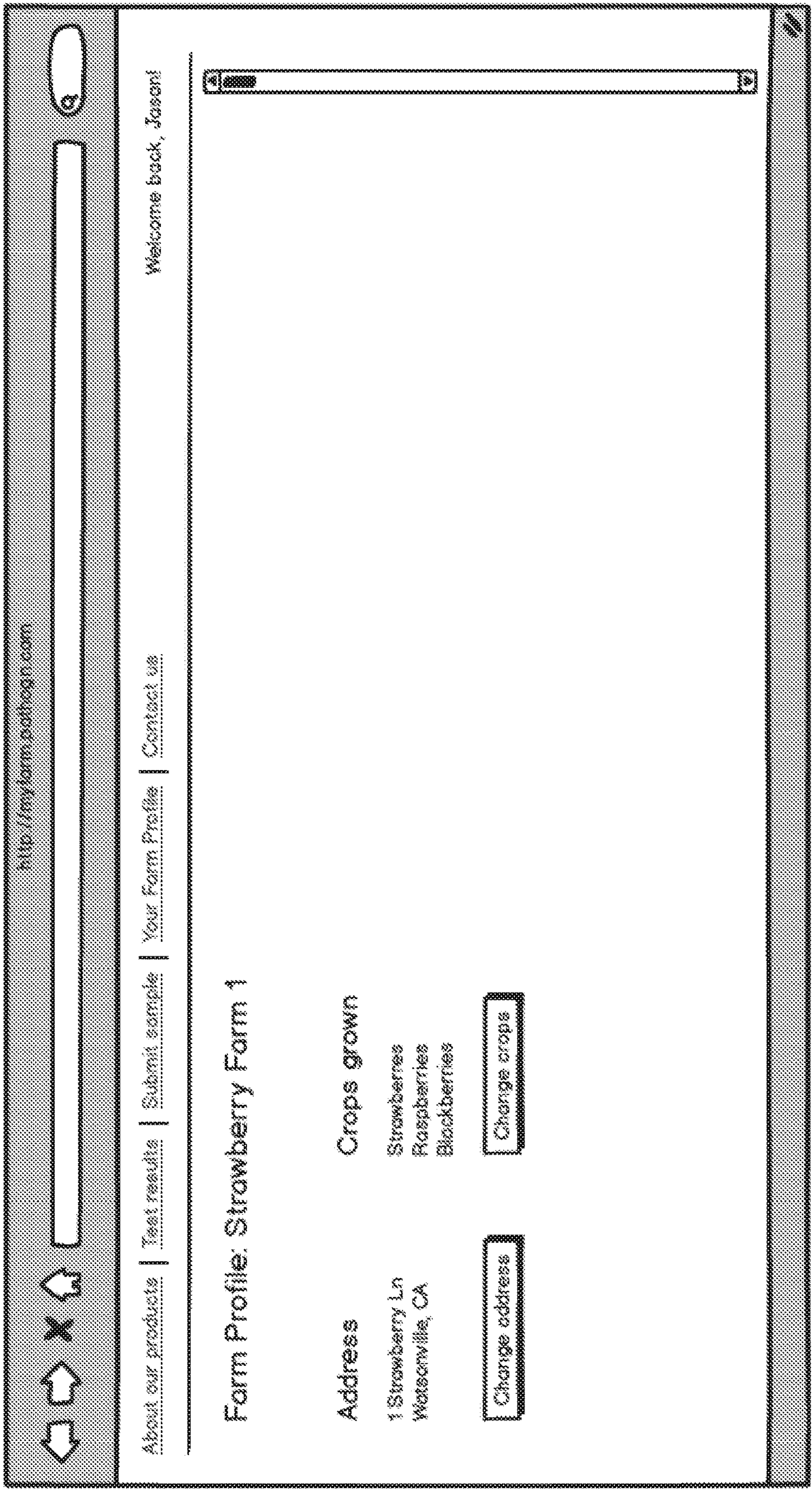
Figure 3G:
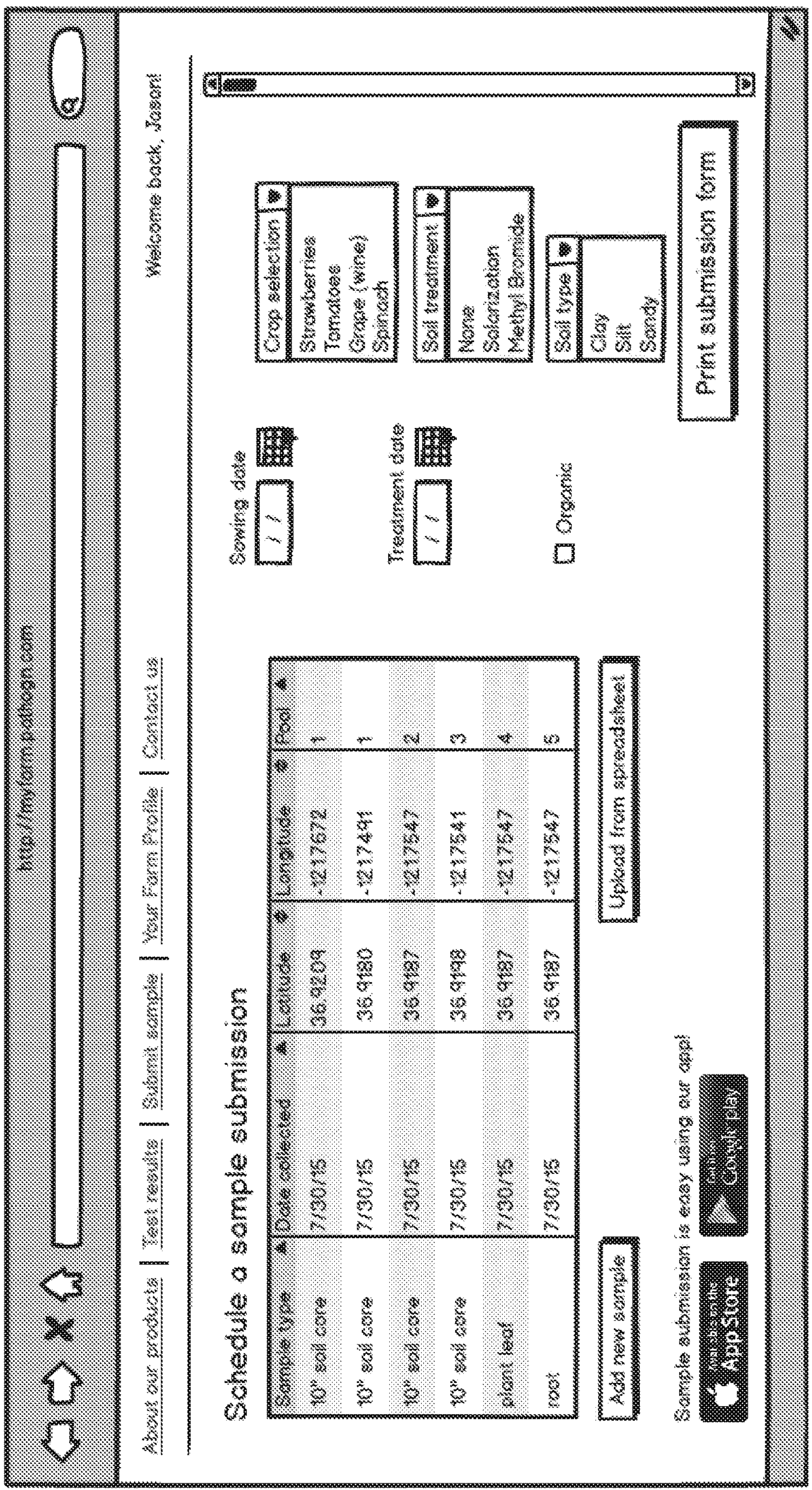

FIG. 2 is a flowchart of one embodiment of a microbe and pathogen predictor utilizing the collective genome of a sample to more accurately predict the presence or absence of a particular microbe in an environment represented by the sample.

Microbe and pathogen predictor 205 receives digitized bioanalysis results in step 210. The collective genome of the sample is determined in step 214. Because both known and unknown microbes (from aligned and unaligned sequences) are represented in the collective genome, more information is available for the microbe and pathogen prediction.

The collective genome is applied to the learning system in step 216. The precise identity of causal organisms is not known for many diseases. The learning system is able to utilize the nucleic acid sequences found in the sample, along with information about aligned microbes and known pathogens found in the collective genome, to make a prediction about the likelihood of one or more pathogens present in the environment represented by the sample in step 218. The learning system may also determine the single microbe or combination of microbes driving symptoms of the disease.

Not only may the presence of a particular microbe of concern be predicted by finding at least a threshold amount of that microbe in the sample, but the learning system may use stochastic analysis of populations in the collective genome to predict the presence of that microbe even without finding that microbe present. For example, a collection of unaligned nucleic acid sequences in the collective genome for the sample may have a high correlation with the presence (or absence) of the particular microbe of concern. For some microbes, different strains exist. Such strains have the majority of their sequences identical, but differ in a small portion of their genome. In this situation, the strains may include pathogenic and non-pathogenic microbes, and they may carry differences in their genetic material. For example, pathogenic and non-pathogenic microbes could be distinguished by the absence or presence of specific loci, or variation in the copy number of the loci, or variation in the nucleotide sequence of the loci (where loci may mean individual nucleotides, portions of genes, entire genes, noncoding regions, etc.), such that these differences may have pathogenic, beneficial or neutral implications for the microbe's interaction with other biotic and abiotic entities.

The learning system may be used to distinguish between pathogenic and non-pathogenic microbes with a majority identical sequence.

Utilizing the additional information of unaligned sequence associations in the pathogen and other microbe detector in addition to the aligned sequence information allows a more nuanced indicator of pathogens and other microbes in samples than has heretofore been available, whether or not the microbe itself is present and sequenced properly in the sample. The learning system not only enables a better prediction of the presence or absence of certain microbes, it also improves detection based on multiple samples from multiple sources to adjust predictions. In some embodiments, the learning system may indicate that additional samples should be taken to increase the sensitivity of the pathogen and other microbe detector.

Additional information in step 212 may also be applied to the learning system in step 216 to further improve the stochastic analysis of the learning system. Such additional information may include metadata such as operational data about a farm (such as the length of time in operation, source of the seeds for the farm, other farms utilizing those seeds, personnel managing the farm, prior farms managed by one or more personnel may be relevant), location data (such as latitude & longitude, climate, weather patterns, sources of water), and use data (fertilizer use, pesticide use), etc. As the learning system improves with each analysis of each sample, the predictive behavior of the learning system improves. Note that with the collective genome, we don't need to study individual unaligned sequences or align unaligned sequences to known microbes. Any microbe may be detected in this way, such as citrus greening or strawberry disease. In one embodiment, a single soil sample may be analyzed for multiple microbe presences.

In some embodiments, learning system 216 uses the additional information applied 212 and the collective genomes from a plurality of samples to determine additional issues of interest. Unaligned sequences in a sample may also be predictive of other traits. For example, a combination of unaligned sequences may be predictive of crop stress, yield, propagative state, nutritional state, etc. Additional information may be included to further hone the pathogen and other microbe detector. In some embodiments, this information is in the form of metadata significant to a relevant sample. All of the relevant information and analytics may be stored in a database at step 220.

Figure 4A:
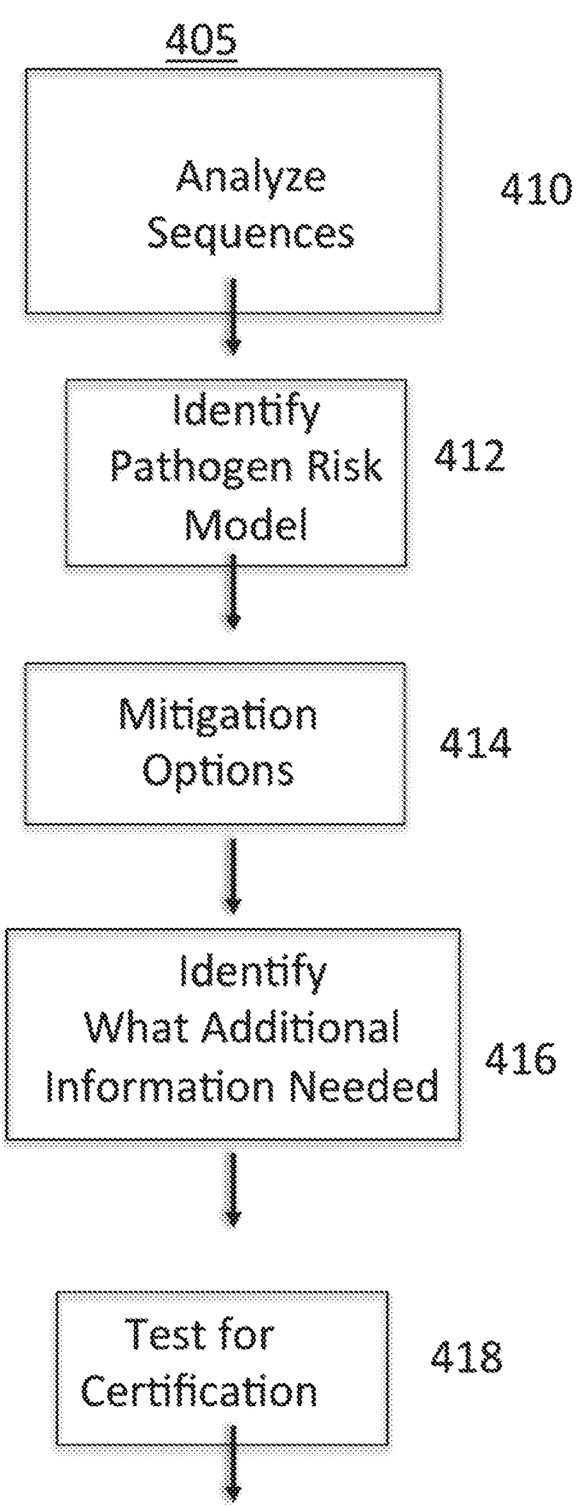
FIG. 4A is a flowchart of one embodiment of certification for the present nucleotide analysis system.

FIG. 4A is a flowchart of one embodiment of the learning system in accordance with the present invention. Learning system 405 analyzes sample sequence information and may incorporate sequence information from other samples to provide insight into the contents of the sample and the likelihood to contain pathogens or other microbes. Information about sample sequences is collected from a digitizer or database in step 410 and analyzed. That information is used to determine a risk of pathogens or other microbes in step 412. The presence of such pathogens or other microbes, metadata, the planting settings (what will be planted and when) are used to calculate the predicted risk of one or more pathogens. In one embodiment, the prediction has an associated prediction confidence. In one embodiment, the user may recalculate the risk, changing planting settings. For such a recalculation, the pathogen profile doesn't change.

Given information in the sample and information from a database on other samples and the predicted risk, in one embodiment, mitigation options are determined in step 414.

If additional information is needed, it is identified in step 416. In one embodiment, a report or certification is provided in step 418.

Figure 4B:
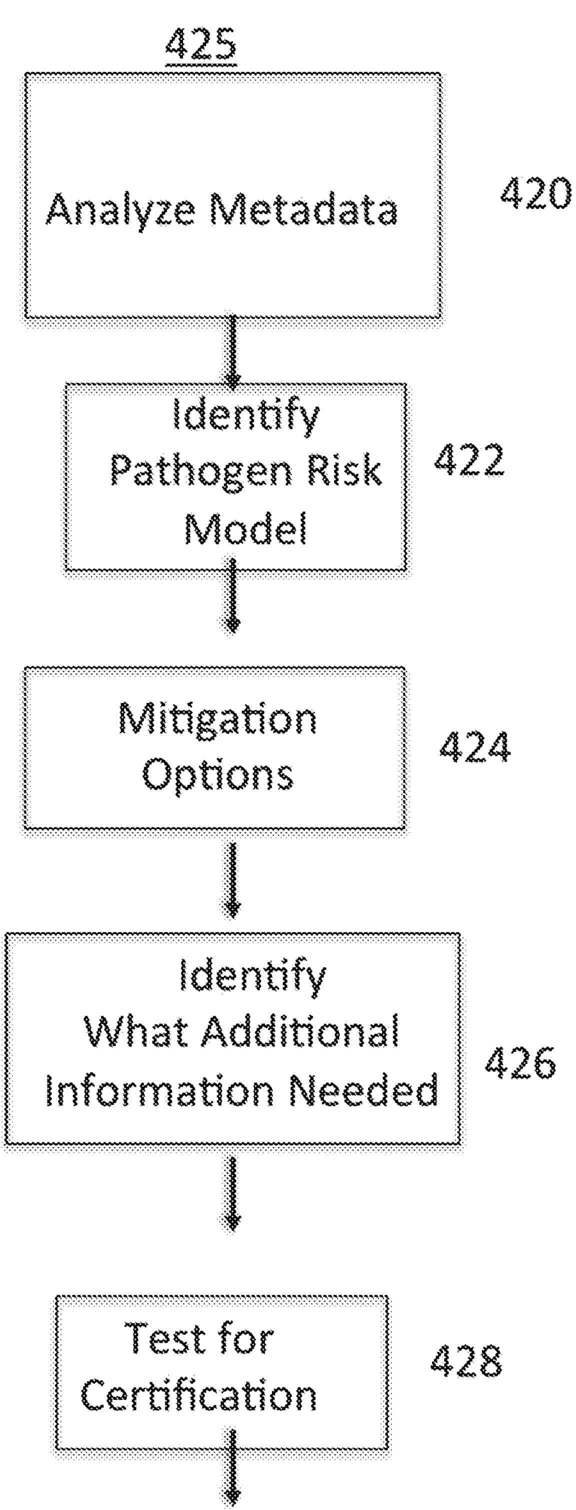
FIG. 4B is a flowchart of one embodiment of the learning system in accordance with the present invention.

FIG. 4B is a flowchart of one embodiment of the learning system in accordance with the present invention. Learning system 425 analyzes metadata in addition to sequence information for a sample, as well as information related to other samples and their associated sequences and metadata, to provide insights into the contents of the sample and the likelihood of pathogens or other microbes. Metadata relevant to potential microbes tested-for may be collected in step 420. The metadata may include, for example, operational data about a farm, such as the length of time in operation, source of the seeds for the farm, other farms utilizing those seeds, personnel managing the farm, prior farms managed by one or more personnel. Other data, such as latitude & longitude, weather patterns, sources of water, fertilizer use, pesticide use, etc. may also be collected as part of the metadata. In one embodiment, the system can utilize whatever metadata is available. In one embodiment, the system may create structured metadata describing factors that may impact microbe presence, from the collected data.

In step 422, the likelihood of a pathogen being present is calculated utilizing the metadata. This will be described in more detail below.

In some embodiments of the present invention, options for mitigating the risk are calculated in step 424. For example, the likelihood of a microbe being present in a sample may trigger a suggestions for reducing the quantity of that microbe in the source from which the sample originated. In some embodiments, the learning system builds a model of the disease risk posed by the nucleic acid molecules present in the sample, thereby determining disease risk factors that may contribute to the disease. These disease risk factors (e.g., raw nucleotides, genes, or organisms), may be targeted in treatments for the disease. In some embodiments, the learning system may indicate that additional samples should be taken to increase the sensitivity of the pathogen and other microbe detector, as noted in step 426. Other data which may be requested includes additional metadata.

In some embodiments, a pathogen or other microbe geomodel is created to indicate localized risk associated with the microbe, such as in a geospatial or temporal heat map. Information stored within the database, as samples are analyzed and incorporated into the database, provide additional context for the analysis that is being done.

In some embodiments, seed farms may utilize the pathogen or other microbe detector for determining both a risk for one or more microbes and have a genomic assessment, for example, for a certification that the seed farm is unlikely to have the presence of one or more microbes, such as in step 428. In some embodiments, seed farms may utilize the pathogen or other microbe detector for determining a risk for one or more microbes in their seeds as well as the soil on which the seeds will be planted. The geomodel may be used to incorporate geographical climate, soil nutrients, metabolites, farming history, host genetics and other information (collectively metadata) to calculate a holistic risk for diseases given the combination of pathogens present on the seed and on the seed lot and the metadata.

Familial relationships of unaligned microbiome sequences may be made through a study known as epidemiology. In some embodiments, predictions of familial relationships of unaligned sequences are made. Expanding on the microbiome techniques, studies may be made of the pathigenome, or the family relationships of microbes. For example, closely related unaligned sequences from one or more samples might be predictively analyzed to conclude the unaligned sequences are mutations of each other or even of aligned sequences. Mapping the path of these mutations may show where a microbe originated.

In this way, sequencing populations, such one or more of a population of microbes or unaligned sequences, enables the use of novel stochastic techniques to give better statistical strength than single sequence based epidemiology.

Figure 5A:
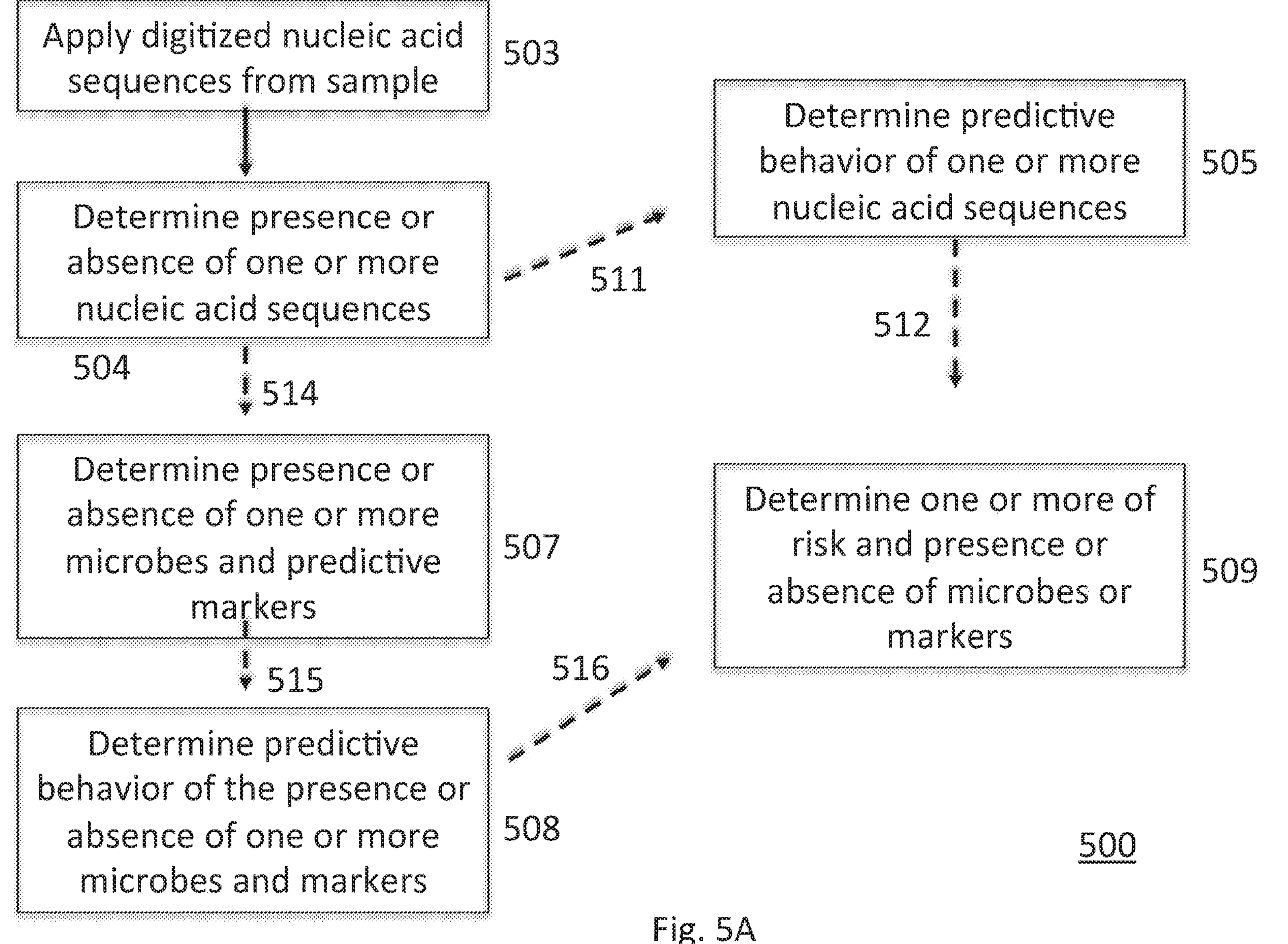
FIG. 5A is a flowchart of one embodiment of one or more learning systems of the nucleotide analysis system.

FIG. 5A is a flowchart of one embodiment of identify predictive behavior using a learning system. A sample of digitized nucleic acid sequences are applied to the learning system(s) in step 503. As noted above, this sample includes a whole host of microbes. These nucleic acid sequences are analyzed to determine the presence or absence of one or more nucleic acid sequences in step 504. When following possible path 511, the learning system(s) determine the predictive effect of one or more nucleic acid sequences in step 505 from the nucleic acid sequences determined in step 504. For example, a set of one or more nucleic acid sequences might correlate to the presence of a particular microbe, or might correlate to a predictive marker such as a by-product of one or more microbes, or correlate to disease. For example, if a nucleic acid sequence is consistently present when citrus greening is found, the sequence may be associated with citrus greening, even if it does not occur within the actual microbes responsible for that disease. In one embodiment, the more frequently such co-occurrence happens the stronger the deduced correlation, and the more likely that the learning system will flag the nucleic acid sequence as being strongly correlated to citrus greening.

Alternately or additionally, when following path 514, the nucleic acid sequences determined in step 504 are used to determine the presence or absence of one or more microbes and markers in step 507. For example, a set of one or more nucleic acid sequences might indicate the presence of a particular microbe or a marker. When following path 515, the presence or absence of one or more microbes and markers in the sample from 507 may be used to determine the predictive behavior of the presence or absence of one or more microbes and markers in step 508. From either step 508 when following path 516 or step 505 from following path 512, one or more of the risk and presence or absence of microbes or markers may be determined in step 509

Figure 5B:
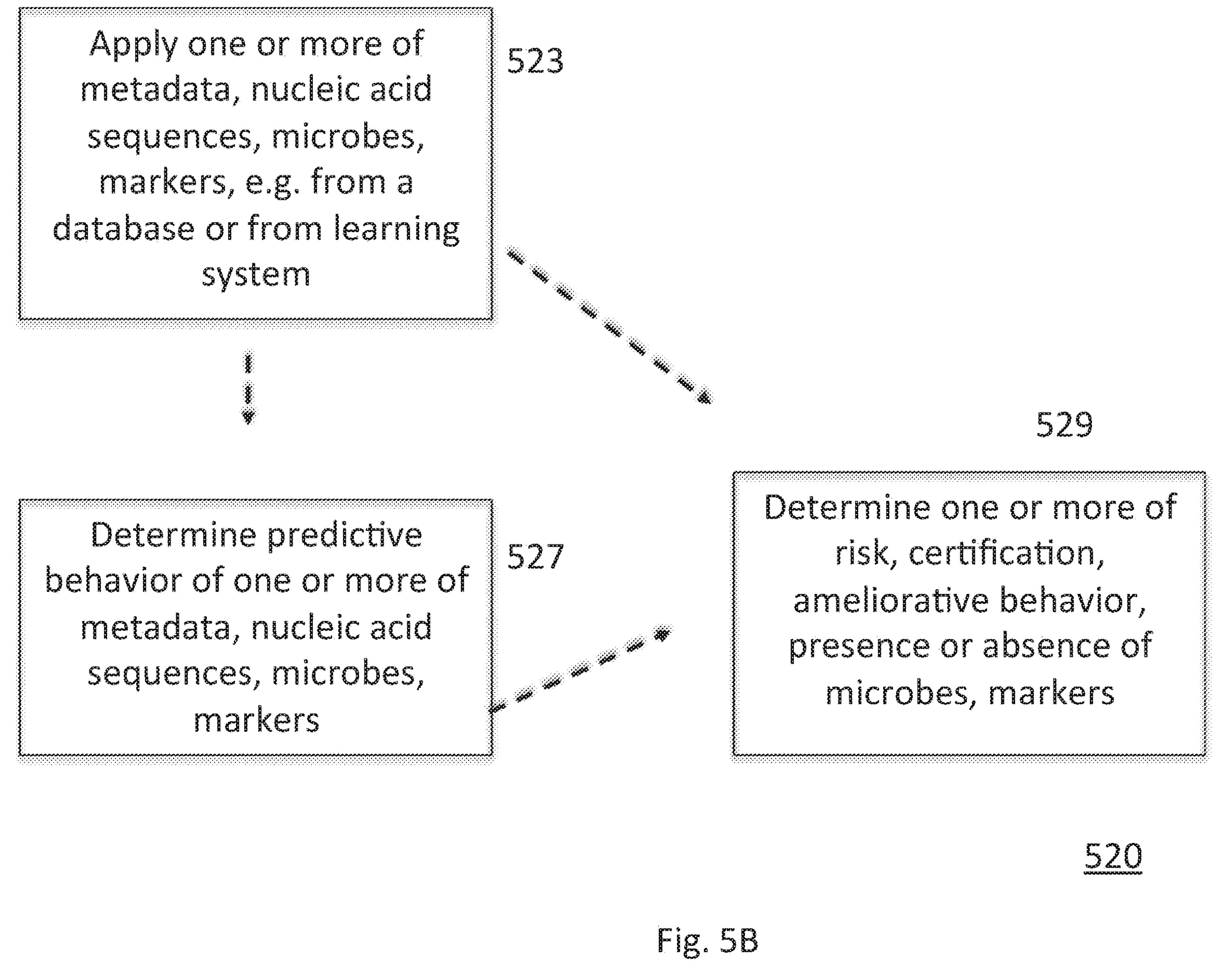
FIG. 5B is a flowchart of one embodiment of one or more learning systems of the nucleotide analysis system.

FIG. 5B is a flowchart of one embodiment of one or more learning system(s) 520 of the nucleotide analysis system. Information such as one or more of metadata, nucleic acid sequences, microbes, markers are applied in step 523. For example, this information may be applied from a database or from learning system 500. In one path, predictive behavior of one or more of metadata, nucleic acid sequences, microbes and markers are determined in step5 527. From either the information in step 523 or the predictive behavior in step 527, learning system 520 determines one or more of risk, such as the risk of disease or the presence or absence of microbes, a certification, possible ameliorative behavior or the presence or absence of microbes and markers.

Figure 5C:
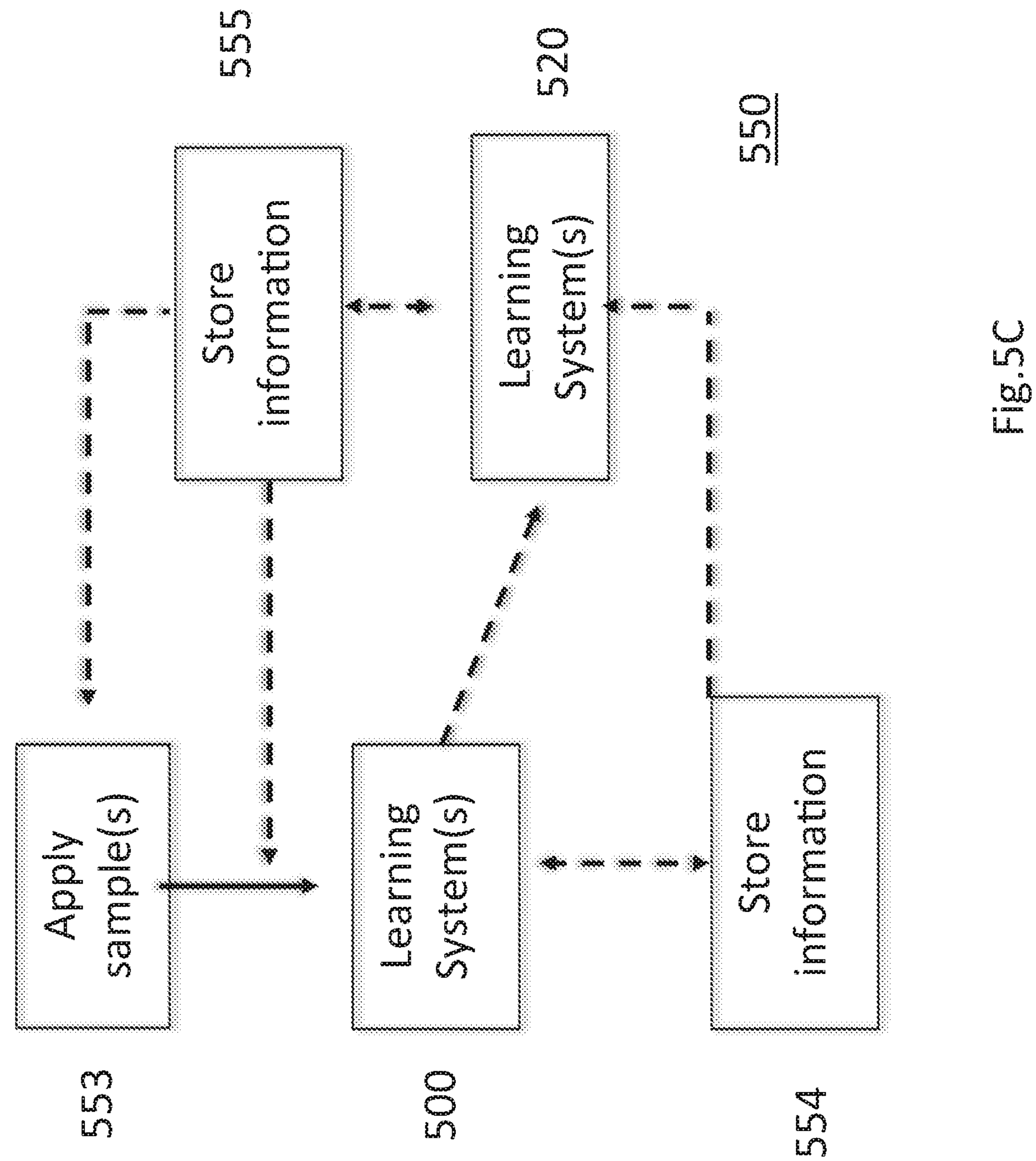
FIG. 5C is a flowchart of one embodiment of the nucleotide analysis system.

FIG. 5C is a flowchart of one embodiment of the nucleotide analysis system. Nucleotide analysis system 550 may take applied samples in step 553 or information already known, such as from information storage in step 555, and apply it to one or more learning systems, such as learning system(s) 500 in FIG. 5A. Information from learning system(s) 500 may be stored or retrieved, e.g. in database 150 in FIG. 1, or applied to one or more learning systems, such as learning system(s) 520 in FIG. 5B.

Figure 6:
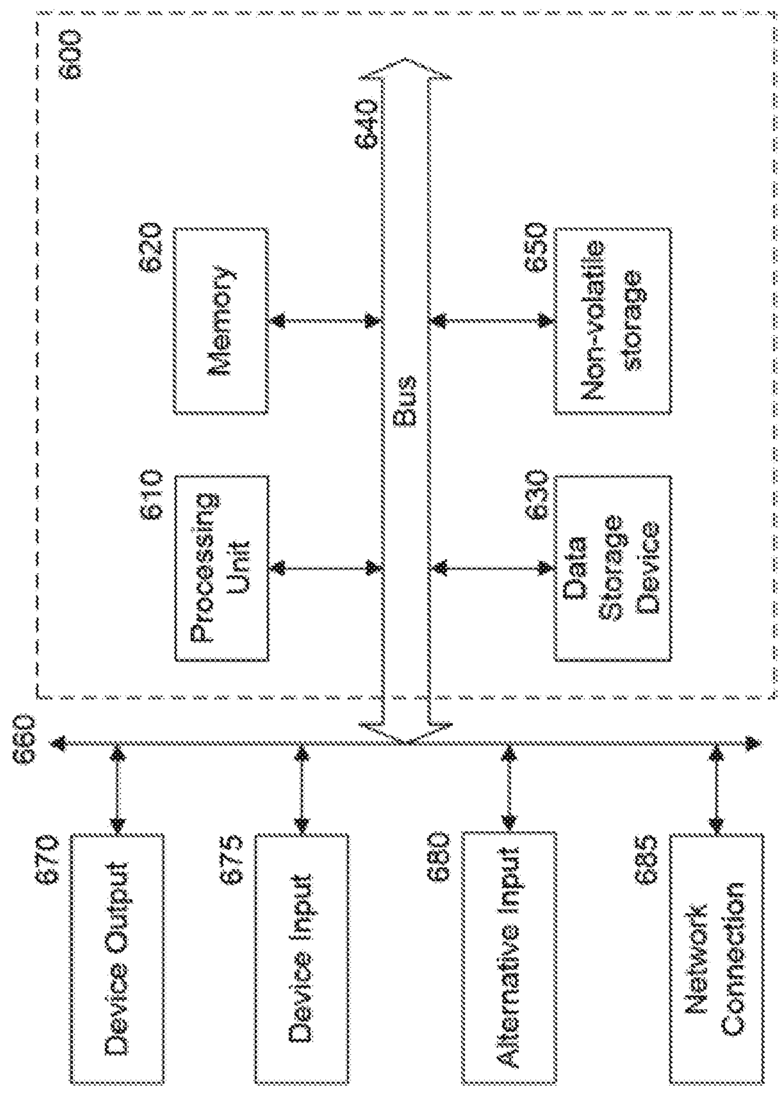
FIG. 6 is a block diagram of one embodiment of a computer system that may be used with the present invention.

Information from learning system(s) 520 may be stored or retrieved, e.g. in database 150. Nucleotide analysis system 550 may iterate on information already known, apply additional sample(s) 553. In this way, nucleotide analysis system 550 may predict risk such as risk of disease, and also may predict indicators of risk, such as risk of disease. For example, a combination of particular microbes and a particular climate may be a higher risk for a particular disease than the same particular microbes in a different climate. In another example, a set of high risk factors may be rendered low risk by the presence of ameliorative microbes also present in the sample. In another example, a pathogen may be found to affect one type of host and not another. Risks such as these may be determined by nucleotide analysis system 550, for example, by the nucleotide sequences alone or by combinations of microbes found from the nucleotide sequences, or by other means disclosed herein, whether or not microbes are determined and whether or not they are aligned or unaligned. In other words, in some embodiments, nucleotide analysis system 550 may determine one or more of causal factors for a disease, modulators of the disease, and beneficial microbes that are suppressors of the disease FIG. 6 is a block diagram of one embodiment of a computer system that may be used with the present invention. It will be appreciated by those of ordinary skill in the art that any configuration of the particular machine implemented as the computer system may be used according to the particular implementation. The control logic or software implementing the present invention can be stored on any machine-readable medium locally or remotely accessible to a processor. A machine-readable medium includes any mechanism for storing information in a form readable by a machine (e.g. a computer). For example, a machine readable medium includes read-only memory (ROM), random access memory (RAM), magnetic disk storage media, optical storage media, flash memory devices, or other storage media which may be used for temporary or permanent data storage. In one embodiment, the control logic may be implemented as transmittable data, such as electrical, optical, acoustical or other forms of propagated signals (e.g. carrier waves, infrared signals, digital signals, etc.).

In some embodiments, the responsiveness of individual plants to a microbe can be used to look for resistance to that microbe on a quantifiable level, rather than just by appearance. In some embodiments, earlier detection of microbes may be possible. In some embodiments, if a greater resistance is shown to the microbe by an individual plant, whether or not the plant is completely resistant to the microbe, that plant may be bred before it dies. After several generations, it is possible that the slight resistance shown by the earlier plants may be bred into a greater resistance by later generations. Novelly, this allows the ability to breed for a trait that isn't actually present in the population.

What is claimed is:

1. A computer-implemented method of training a model for prediction of disease risk in soil, comprising:

receiving digitized samples of a plurality of soil samples, the digitized samples including a plurality of sets of nucleic acid sequences of microbes present in the plurality of soil samples, wherein each of the plurality of sets of nucleic acid sequences is associated with a different one of the plurality of soil samples;

determining that at least one of the plurality of sets of nucleic acid sequences includes an unaligned sequence, wherein the unaligned sequence is a nucleic acid sequence that does not align within a threshold number of nucleotides to nucleotides of any known nucleic acid sequences of one or more known microbes predictive of a disease;

determining, for each of the plurality of sets of nucleic acid sequences, whether there is a co-occurrence of (i) a set of nucleic acid sequences of the plurality of sets of nucleic acid sequences including at least the unaligned sequence and (ii) the disease present in a soil sample of the plurality of soil samples associated with the set of nucleic acid sequences;

creating a training data set by associating with the disease the unaligned sequence responsive to determining the co-occurrence for a threshold number of the plurality of sets of nucleic acid sequences; and training the model using the training data set to predict risk of the disease in a test soil sample, wherein the model accounts for a presence of an ameliorative microbe in the test soil sample that reduces the risk of the disease, and wherein the model learns a predictive effect of co-occurrence of the unaligned sequence and the ameliorative microbe on the risk of the disease.

2. The method of claim 1, further comprising:

determining that the unaligned sequence does not correlate to a by-product of the one or more known microbes predictive of the disease.

3. The method of claim 1, further comprising:

training the model with metadata describing a location where the plurality of soil samples is obtained.

4. The method of claim 1, further comprising:

training the model with metadata including one or more of weather patterns, sources of water, fertilizer use, pesticide use, source of seeds, and operational data about a farm from which the plurality of soil samples is sourced.

5. The method of claim 1, further comprising:

determining that the unaligned sequence does not align within a threshold number of nucleotides to the nucleotides of any known nucleic acid sequences by determining absence of a specific loci in the unaligned sequence.

6. The method of claim 1, wherein the model is a multi-layered neural network, and wherein the model takes input nucleic acid sequences and outputs phenotypic characteristics.

7. The method of claim 1, wherein the disease is citrus greening or strawberry disease.

8. The method of claim 1, further comprising:

determining that the plurality of sets of nucleic acid sequences includes a different nucleic acid sequence that aligns to at least one of the nucleotides of one or more known nucleic acid sequences of the one or more known microbes predictive of the disease; and determining that presence of the different nucleic acid sequence is predictive of the disease.

9. The method of claim 1, further comprising:

determining that the plurality of sets of nucleic acid sequences includes a different nucleic acid sequence that aligns to nucleotides of nucleic acid sequences of a microbe known to be a suppressor of at least one disease.

10. The method of claim 1, further comprising:

providing an alert regarding a prediction of the model.

11. The method of claim 1, wherein the digitized samples are received from a sequencer.

12. A system for training a model for prediction of disease risk in soil, comprising:

a non-transitory computer-readable storage medium storing instructions, the instructions when executed by one or more processors cause the one or more processors to:

receive digitized samples of a plurality of soil samples, the digitized samples including a plurality of sets of nucleic acid sequences of microbes present in the plurality of soil samples, wherein each of the plurality of sets of nucleic acid sequences is associated with a different one of the plurality of soil samples;

determine that at least one of the plurality of sets of nucleic acid sequences includes an unaligned sequence, wherein the unaligned sequence is a nucleotide sequence that does not align within a threshold number of nucleotides to nucleotides of any known nucleic acid sequences of one or more known microbes predictive of a disease;

determine, for each of the plurality of sets of nucleic acid sequences, whether there is a co-occurrence of (i) a set of nucleic acid sequences of the plurality of sets of nucleic acid sequences including at least the unaligned sequence and (ii) the disease present in a soil sample of the plurality of soil samples associated with the set of nucleic acid sequences;

create a training data set by associating with the disease the unaligned sequence responsive to determining the co-occurrence for a threshold number of the plurality of sets of nucleic acid sequences; and train the model using the training data set to predict risk of the disease in a test soil sample, wherein the model accounts for a presence of an ameliorative microbe in the test soil sample that reduces the risk of the disease, and wherein the model learns a predictive effect of co-occurrence of the unaligned sequence and the ameliorative microbe on the risk of the disease.

13. The system of claim 12, wherein the one or more processors are further configured to:

determine that the unaligned sequence does not correlate to a by-product of the one or more known microbes predictive of the disease.

14. The system of claim 12, wherein the one or more processors are further configured to:

train the model with metadata describing a location where the plurality of soil samples is obtained.

15. The system of claim 12, wherein the one or more processors are further configured to:

train the model with metadata including one or more of weather patterns, sources of water, fertilizer use, pesticide use, source of seeds, and operational data about a farm from which the plurality of soil samples is sourced.

16. The system of claim 12, wherein the one or more processors are further configured to:

determine that the unaligned sequence does not align within a threshold number of nucleotides to the nucleotides of any known nucleic acid sequences by determining absence of a specific loci in the unaligned sequence.

17. The system of claim 12, wherein the model is a multi-layered neural network, and wherein the model takes input nucleic acid sequences and outputs phenotypic characteristics.

18. The system of claim 12, wherein the disease is citrus greening or strawberry disease.

19. The system of claim 12, wherein the one or more processors are further configured to:

determine that the plurality of sets of nucleic acid sequences includes a different nucleic acid sequence that aligns to at least one of the nucleotides of one or more known nucleic acid sequences of the one or more known microbes predictive of the disease; and determine that presence of the different nucleic acid sequence is predictive of the disease.

20. The system of claim 12, wherein the one or more processors are further configured to:

determine that the plurality of sets of nucleic acid sequences includes a different nucleic acid sequence that aligns to nucleotides of nucleic acid sequences of a microbe known to be a suppressor of at least one disease.

* * * * *